(12) United States Patent
Han et al.

(10) Patent No.: US 7,830,522 B2
(45) Date of Patent: Nov. 9, 2010

(54) METHOD AND APPARATUS FOR DETERMINING REFLECTANCE DATA OF A SUBJECT

(75) Inventors: Jefferson Y. Han, Holliswood, NY (US); Kenneth Perlin, New York, NY (US)

(73) Assignee: New York University, New York, NY (US)

( * ) Notice: Subject to any disclaimer, the term of this patent is extended or adjusted under 35 U.S.C. 154(b) by 754 days.

(21) Appl. No.: 11/705,195

(22) Filed: Feb. 12, 2007

(65) Prior Publication Data

US 2007/0216905 A1    Sep. 20, 2007

Related U.S. Application Data

(63) Continuation-in-part of application No. 10/665,804, filed on Sep. 19, 2003, now Pat. No. 7,177,026.

(60) Provisional application No. 60/476,320, filed on Jun. 6, 2003, provisional application No. 60/413,533, filed on Sep. 25, 2002.

(51) Int. Cl.
 *G01N 21/47* (2006.01)
 *G01N 21/55* (2006.01)
(52) U.S. Cl. ...................... 356/446; 356/445
(58) Field of Classification Search ........ None
 See application file for complete search history.

(56) References Cited

U.S. PATENT DOCUMENTS

| 5,517,315 | A | * | 5/1996 | Snail et al. ............... 356/445 |
| 5,637,873 | A | * | 6/1997 | Davis et al. ............ 250/339.11 |
| 6,122,042 | A | | 9/2000 | Wunderman et al. |
| 2004/0036882 | A1 | | 2/2004 | Perlin |
| 2004/0061784 | A1 | | 4/2004 | Perlin |
| 2005/0068537 | A1 | | 3/2005 | Han et al. |

FOREIGN PATENT DOCUMENTS

DE    10143602 A1    4/2003

* cited by examiner

*Primary Examiner*—Gregory J Toatley, Jr.
*Assistant Examiner*—Amanda H Merlino
(74) *Attorney, Agent, or Firm*—Ansel M. Schwartz

(57) ABSTRACT

An apparatus for obtaining reflectance data of an object includes a diffuser having a surface. The apparatus includes a mapping portion that effects a mapping between a light field at the object's surface and a light field at the diffuser surface for BRDF capture of the object. A method for obtaining reflectance data usable to determine a plurality of values of the BRDF of an object. The method includes the steps of illuminating the object. There is the step of effecting a mapping between a light field at the object's surface and a light field at a diffuser surface for BRDF capture of the object with a mapping portion. An apparatus and a method for measuring an 8D reflectance field of an object or a 3D object.

40 Claims, 10 Drawing Sheets

METHOD AND APPARATUS FOR DETERMINING REFLECTANCE DATA OF A SUBJECT

This application claims the benefit of U.S. Provisional Application No. 60/476,320 filed on Jun. 6, 2003. This application is a continuation-in-part of application Ser. No. 10/665,804 filed on Sep. 19, 2003 now U.S. Pat. No. 7,177,026, which claims the benefit of U.S. Provisional Application No. 60/413,533 filed on Sep. 25, 2002.

FIELD OF THE INVENTION

The present invention is related to determining reflectance data of a subject. More specifically, the present invention is related to determining reflectance data of a subject using a kaleidoscope. The reflectance data may consist of one or more values of a bi-directional reflectance distribution function (BRDF), a bi-directional texture function (BTF), an 8 dimension reflectance field and/or a bi-directional scattering surface texture function (BSSTF).

BACKGROUND OF THE INVENTION

Much recent work in realistic image synthesis has focused on the use of actual data measurements of real-world surfaces and materials, both in the search for better data-driven reflectance models, and for direct use in image-based rendering techniques.

The reflectance properties of a surface can be characterized by its Bidirectional Reflectance Distribution Function (BRDF) [NICODEMUS, F. E., RICHMOND, J. C., AND HSIA, J. J. 1977. Geometric Considerations and Nomenclature for Reflectance, U.S. Dept. of Commerce, National Bureau of Standards, October 1977, incorporated by reference herein], the four dimensional function that describes how much light from any incident direction $(\theta_i, \phi_i)$ is transferred to any exitant direction $(\theta_e, \phi_e)$:

$$BRDF(\theta_i, \phi_i, \theta_e, \phi_e)$$

The field is quite mature in techniques for measuring BRDFs, and for representing them accurately and compactly. Real world surfaces, however, are not perfectly homogeneous—they exhibit local variations in microgeometry and in reflectance, which are not adequately represented by a single BRDF.

Dana et al. define the Bidirectional Texture Function (BTF) as the six dimensional function which extends the BRDF by allowing reflectance to vary spatially along the surface, parameterized by (u,v) DANA, K. J., GINNEKEN, B. VAN, NAYAR, S. K., AND KOENDERINK, J. J. 1999. Reflectance and Texture of Real World Surfaces. ACM Transactions on Graphics, 18, 1, 1-34, incorporated by reference herein:

$$BRDF(u, v, \theta_i, \phi_i, \theta_e, \phi_e)$$

This representation is able to effectively capture the various subtleties of complexly textured surfaces, particularly those exhibiting such phenomena as self-occlusion and self-shadowing.

There have been recent advances in working with BTFs for realistic image synthesis. Because the BTF is a large unwieldy 6D function, it is difficult to obtain a dense sampling, and therefore current databases are relatively sparse. Yet recent successful research has shown that even a sparse sampling of the BTF can be adequate for rendering applications. LIU, X., YU, Y., AND SHUM, H. Y. 2001. Synthesizing Bidirectional Texture Functions for Real-World Surfaces. In Proceedings of ACM SIGGRAPH 2001, ACM Press/ACM SIGGRAPH, New York. E. Fiume, Ed., Computer Graphics Proceedings, Annual Conference Series, ACM, 97-106; TONG, X., ZHANG, J., LIU, L., WANG, X., GUO, B., AND SHUM, H. Y. 2002. Synthesis of Bidirectional Texture Functions on Arbitrary Surfaces. ACM Transactions on Graphics, 21, 3, 665-672; VASILESC, M. A. O., AND TERZOPOULOS, D. 2003. TensorTextures. ACM SIGGRAPH 2003 Conference Abstracts and Applications, July 2003, all of which are incorporated by reference herein.

Increased quality of BTF sample data would also be of benefit to computer vision research. For example, algorithms that reconstruct geometry or motion from multiple views require correspondences to be found between these views. BTF data would allow robust testing of the identification of corresponding surface points, even as the appearance of each surface point varies with view angle. This data would also benefit shape-from-texture, texture segmentation, and texture recognition techniques.

Use of real-world reflectance is currently characterized by the difficulty of gathering the BRDF and the BTF, particularly due to the high dimensionality of this data.

The straightforward approach to measuring the 4D BRDF is to mechanically position a light source and photometer around the hemisphere about the sample though the use of robotic armatures, as in Murray-Coleman and Smith. MURRAY-COLEMAN, J. F., AND SMITH, A. M. 1990. The Automated Measurement of BRDFs and their Application to Luminaire Modeling. Journal of the Illuminating Engineering Society, pp. 87-99, Winter 1990, incorporated by reference herein. Any such mechanical arrangement must have four degrees of freedom; data collection is tediously performed by sequentially stepping through each position.

Subsequent methods greatly improve the efficiency of data acquisition by reducing the number of mechanically scanned dimensions through the use of a 2D imaging element such as a CCD camera. Ward's LBL imaging gonioreflectometer uses a hemi-ellipsoidal mirror. WARD, G. J. 1992. Measuring and Modeling Anisotropic Reflection. In Computer Graphics (Proceedings of ACM SIGGRAPH 92), 26, 2, ACM, 255-263, incorporated by reference herein. A CCD camera equipped with a wide-angle-lens, and the surface sample are positioned at the mirror's two respective foci to effectively map pixel position to exitant angular position. This method requires mechanical repositioning of the light source. Also notable about Ward's device is that the mirror is semi-transparent, thereby permitting measurements when view and illumination angles are coincident. Others have thoroughly explored the various other possible arrangements of curved mirrors and beam splitters. DAVIS, K. J., AND RAWLINGS, D. C. 1997. Directional reflectometer for measuring optical bidirectional reflectance. U.S. Pat. No. 5,637,873, June 1997; MATTISON, P. R., DOMBROWSKI, M. S., LORENZ, J., DAVIS, K., MANN, H., JOHNSON, P., AND FOOS, B. 1998. Hand-held directional reflectometer: an angular imaging device to measure BRDF and HDR in real-time. In Proceedings of SPIE, The International Society for Optical Engineering, Scattering and Surface Roughness II, 3426:240-251, July 1998; and CARTER, R. R., AND PLESKOT, L. K. 1999. Imaging scatterometer. U.S. Pat. No. 5,912,741, June 1999, all of which are incorporated by reference herein.

An alternative way to utilize an imaging element is to measure the BRDF on a curved sample. Lu et al. arranges a sample patch onto a known cylinder. LU, R., KOENDERINK, J. J., AND KAPPERS, A. M. L. 1998. Optical properties (bidirectional reflectance distribution functions) of velvet. Applied Optics, 37, 25, 5974-5984, incorporated by reference herein. Marschner et al. relaxes the sample geometry restriction by utilizing a range scanner, and improves acquisition flexibility by allowing for free positioning of the capture camera. MARSCHNER, S. R., WESTIN, S. H., LAFORTUNE, E. P. F., TORRANCE, K. E., AND GREENBERG, D. P. 1999. Image-based BRDF Measurement Including Human Skin. In Proceedings of the 10th Eurographics Workshop on Rendering, pp. 131-144, June 1999, incorporated by reference herein.

More recent work attempts to recover the BRDF from sampling environments that are even less structured. Boivin and Gagalowicz demonstrate recovering multiple BRDFs from a single photograph, with known geometry and light source positions. BOIVIN, S. AND GAGALOWICZ, A. 2001. Image-Based Rendering of Diffuse, Specular and Glossy Surfaces from a Single Image. In Proceedings of ACM SIGGRAPH 2001, ACM Press/ACM SIGGRAPH, New York. E. Fiume, Ed., Computer Graphics Proceedings, Annual Conference Series, ACM, 107-116, incorporated by reference herein. Ramamoorth and Hanrahan describe a signal processing framework that generalizes the recovery of the BRDF under unknown lighting conditions. RAMAMOORTHI, R. ANDHANRAHAN, P. 2001. A Signal-Processing Framework for Inverse Rendering. In Proceedings of ACM SIGGRAPH 2001, ACM Press/ACM SIGGRAPH, New York. E. Fiume, Ed., Computer Graphics Proceedings, Annual Conference Series, ACM, 117-128, incorporated by reference herein.

The seminal work by Dana et al. on the BTF [1999] presents a 3DOF robotic system that incrementally tilts/rotates a patch of the sample in front of a light source. This method produces 205 total samples of the BTF, with a relatively even distribution of illumination directions, but, due to mechanical limitations, with a limited distribution of viewing angles. It also requires a sample patch of the surface to be affixed to the device, which makes in situ measurements impossible, particularly for skin.

Other research involving BTFs utilizes various other custom gantry rigs, such as that of Furukawa et al., which uses 2 motorized concentric arcs carrying 6 cameras and 6 lights. FURUKAWA, R., KAWASAKI, H., IKEUCHI, K., AND SAKAUCHI, M. 2002. Appearance based object modeling using texture database: Acquisition, compression and rendering. In Proceedings of the 13th Eurographics Workshop on Rendering Techniques, pp. 257-266, 2002, incorporated by reference herein.

Later work by Dana introduces a BTF measurement device that utilizes a concave paraboloid mirror section, similar to that used in previous BRDF capture devices, but in concert with an aperture and a translation stage for the sample. DANA, K. J. 2001. BRDF/BTF Measurement Device. In Proceedings of Eighth IEEE International Conference on Computer Vision (ICCV), IEEE Computer Society, vol. 2, pp. 460-6, Vancouver, British Columbia, July 2001, incorporated by reference herein. Theoretically, this technique should be able to produce very high resolution sampling of the BTF in every dimension, with large flexibility in sample distribution, but at a slow capture rate. It also inherits the problems associated with the need to affix surface samples.

Note that this technique is representative of a general class of solutions to the BTF capture problem, which utilize a 4D BRDF measurement device, mechanically scanning the sample across the device to obtain the additional two dimensions.

Other techniques measure that subset of the BTF for which the viewpoint is fixed, and only illumination is varied.

Debevec et al.'s "Light Stage", constructed to capture the complex reflectance of the human face, mechanically scans a directional light source at relatively high speeds through two degrees of freedom, capturing 64×32 illumination samples. DEBEVEC, P., HAWKINS, T., TCHOU, C., DUIKER, H. P., SAROKIN, W., AND SAGAR, M. 2000. Acquiring the Reflectance Field of a Human Face. In Proceedings of ACM SIGGRAPH 2000, ACM Press/ACM SIGGRAPH, New York. Computer Graphics Proceedings, Annual Conference Series, ACM, 145-156, incorporated by reference herein. Successive versions of the stage have replaced this single light source, first with a linear array of xenon strobes on a motorized arc, and then with a static 2D array of 156 LED clusters, allowing for the capture of subjects in motion under arbitrary illumination conditions. DEBEVEC, P., WENGER, A., TCHOU, C., GARDNER, A., WAESE, J., AND HAWKINS, T. 2002. A Lighting Reproduction Approach to Live-Action Compositing. ACM Transactions on Graphics, 21, 3, 547-556, incorporated by reference herein.

Malzbender et al. describes a device for in situ surface reflectance measurement, wherein 50 inward-pointing light sources are distributed on a small, portable hemispherical frame, allowing for rapid automated acquisition. MALZBENDER, T., GELB, D., AND WOLTERS, H. 2001. Polynomial Texture Maps. In Proceedings of ACM SIGGRAPH 2001, ACM Press/ACM SIGGRAPH, New York. E. Fiume, Ed., Computer Graphics Proceedings, Annual Conference Series, ACM, 519-528, incorporated by reference herein. Polynomial curves are fitted to the lighting-dependent color at each pixel; these curves are used to generate images with novel lighting conditions that interpolate the light positions that were sampled.

The reflectance field [Debevec 2000], is an eight dimensional function that completely describes the geometric relationship between a ray of light and a textured surface: two dimensions to describe the ray's angle of incidence, two for the exitant angle, two for the position of the surface point on the texture surface, and two for the positional shift of the ray between entering and leaving the surface due to subsurface scattering.

The term Bidirectional Reflectance Distribution Function (BRDF) was first coined by Nicodemus [Nicodemus 1977] to describe the four dimensional relationship between incident and exident light at a surface point.

Dana extended this to six dimensions, coining the term Bidirectional Texture Function (BTF) to account for the two additional dimensions of spatial variance across a texture surface [Dana et al. 1997].

Jensen pointed out that light can enter and exit at different points due to subsurface scattering [Jensen 2001].

Matusik devised a method of measuring and rerendering the analog of the six dimensional BTF for solid objects [Matusik et al. 2002].

Masselus keeps the camera fixed, while allowing lighting direction to vary. This work also used projectors as space-varying light sources for measurement [Masselus et al. 2003] as did [Han and Perlin 2003].

Levoy has also noted that an image can be used as a angularly variant light source for surface reflectance measurement [Levoy 2000].

SUMMARY OF THE INVENTION

The present invention pertains to an apparatus for determining a bidirectional reflectance distribution function of a subject. The apparatus comprises a light source for producing light. The apparatus comprises means for measuring the bidirectional reflectance distribution function of the subject from multiple locations simultaneously with the light.

The present invention pertains to an apparatus for determining a bidirectional reflectance distribution function of a subject. The apparatus comprises a light source for producing light. The apparatus comprises means for measuring the bidirectional reflectance distribution function of the subject from more than 1 camera or more than 1 projector.

The present invention pertains to a method for determining a bidirectional reflectance distribution function of a subject. The method comprises the steps of producing light from a light source. There is the step of measuring the bidirectional reflectance distribution function of the subject from multiple locations simultaneously with the light.

The present invention pertains to an apparatus for determining sub-surface scattering of a subject. The apparatus comprises a light source for producing light. The apparatus comprises means for measuring the sub-surface scattering of the subject.

The present invention pertains to a method for determining sub-surface scattering of a subject. The method comprises the steps of producing light from a light source. There is the step of measuring the sub-surface scattering of the subject.

The present invention pertains to an apparatus for determining sub-surface scattering of a subject. The apparatus comprises a light source for producing light. The apparatus comprises, for a set of incoming light directions and a set of outgoing light directions for each of a set of surface points in regard to the subject; of the light which enters the subject from any incoming light direction from the set of incoming light directions, into any surface point A of the set of surface points, means for measuring a proportion of the light that exits out of the subject in any outgoing light direction of the set of outgoing light directions from surface point B, where points A and B can be either a same point or different points.

The present invention pertains to a method for determining sub-surface scattering of a subject. The method comprises the steps of producing light from a light source. There is the step of, for a set of incoming light directions and a set of outgoing light directions for each of a set of surface points in regard to the subject; of the light which enters the subject from any incoming light direction from the set of incoming light directions, into any surface point A of the set of surface points, measuring a proportion of the light that exits out of the subject in any outgoing light direction of the set of outgoing light directions from surface point B, where points A and B can be either a same point or different points.

The present invention pertains to a technique for measuring the full eight dimensional reflectance field for real world surfaces and objects, and for reconstructing new views of these surfaces under arbitrary lighting conditions.

The present invention pertains to an apparatus for obtaining reflectance data of an object. The apparatus comprises a diffuser having a surface. The apparatus comprises a mapping portion that effects a mapping between a light field at the object's surface and a light field at the diffuser surface for BRDF capture of the object.

The present invention pertains to an apparatus for determining BRDF of an object. The apparatus comprises a light source. The apparatus comprises an image capture portion that captures reflectance data usable to determine a plurality of values of the BRDF in a single image capture.

The present invention pertains to a method for obtaining reflectance data usable to determine a plurality of values of the BRDF of an object. The method comprises the steps of illuminating the object. There is the step of effecting a mapping between a light field at the object's surface and a light field at a diffuser surface for BRDF capture of the object with a mapping portion.

The present invention pertains to an apparatus for measuring an 8D reflectance field of an object, or a 3D object. The apparatus comprises a kaleidoscope having an opening. The apparatus comprises a projector which illuminates the object with a light passing through the kaleidoscope. The apparatus comprises a plurality of cameras dispersed in a staggered arrangement relative to the opening of the kaleidoscope to take images of the surface of the object through the kaleidoscope. At least a portion of the cameras may be angularly staggered relative to the opening of the kaleidoscope.

The present invention pertains to a method for measuring an 8D reflectance field of an object. The method comprises the steps of illuminating the object with light from a projector passing through a kaleidoscope having an opening. There is the step of taking images of the surface of the object through the kaleidoscope with a plurality of cameras dispersed in a staggered arrangement relative to an opening of the kaleidoscope. At least a portion of the cameras may be angularly staggered relative to the opening of the kaleidoscope.

BRIEF DESCRIPTION OF THE DRAWINGS

In the accompanying drawings, the preferred embodiment of the invention and preferred methods of practicing the invention are illustrated in which.

DETAILED DESCRIPTION

Figure 2:
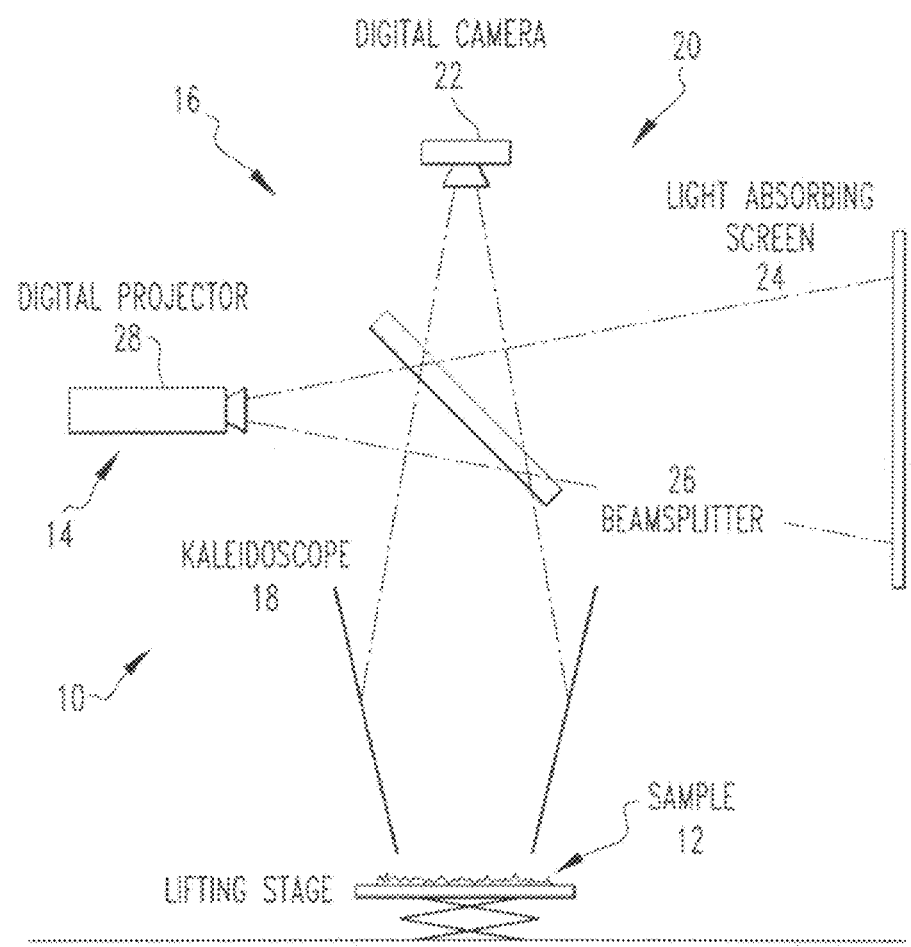
FIG. 2 is a schematic representation of the apparatus of the present invention.

Referring now to the drawings wherein like reference numerals refer to similar or identical parts throughout the several views, and more specifically to FIG. 2 thereof, there is shown an apparatus 10 for determining a bidirectional reflectance distribution function of a subject 12. The apparatus 10 comprises a light source 14 for producing light. The apparatus 10 comprises means 16 for measuring the bidirectional reflectance distribution function of the subject 12 from multiple locations simultaneously with the light.

Preferably, the measuring means 16 includes a kaleidoscope 18. The measuring means 16 preferably includes sensing means 20 for sensing the light from the subject 12. Preferably, the sensing means 20 includes a camera 22 which receives light from the subject 12. The camera 22 is preferably positioned so a path of the light from the subject 12 and the light source 14 are merged.

The sensing means 20 preferably includes a light absorbing screen 24 which receives light from the subject 12. Preferably, the sensing means 20 includes a beam splitter 26 disposed between the camera 22 and a light absorbing screen 24 which allows the light from the subject 12 to be received by both the camera 22 and the light absorbing screen 24. The light source 14 preferably includes a digital projector 28.

The present invention pertains to an apparatus 10 for determining a bidirectional reflectance distribution function of a subject 12. The apparatus 10 comprises a light source 14 for producing light. The apparatus 10 comprises means 16 for measuring the bidirectional reflectance distribution function of the subject 12 using more than 1 camera 22 or more than 1 projector 28.

The present invention pertains to a method for determining a plurality of values of a bidirectional reflectance distribution function of a subject 12. The method comprises the steps of producing light from a light source 14. There is the step of measuring a plurality of values of the bidirectional reflectance distribution function of the subject 12 from multiple locations simultaneously with the light.

The present invention pertains to an apparatus 10 for determining sub-surface scattering of a subject 12. The apparatus 10 comprises a light source 14 for producing light. The apparatus 10 comprises means 16 for measuring the sub-surface scattering of the subject 12.

The present invention pertains to a method for determining sub-surface scattering of a subject 12. The method comprises the steps of producing light from a light source 14. There is the step of measuring the sub-surface scattering of the subject 12.

The present invention pertains to an apparatus 10 for determining sub-surface scattering of a subject 12. The apparatus 10 comprises a light source 14 for producing light. The apparatus 10 comprises, for a set of incoming light directions and a set of outgoing light directions for each of a set of surface points in regard to the subject 12; of the light which enters the subject 12 from any incoming light direction from the set of incoming light directions, into any surface point A of the set of surface points, means 16 for measuring a proportion of the light that exits out of the subject 12 in any outgoing light direction of the set of outgoing light directions from surface point B, where points A and B can be either a same point or different points.

The present invention pertains to a method for determining sub-surface scattering of a subject 12. The method comprises the steps of producing light from a light source 14. There is the step of, for a set of incoming light directions and a set of outgoing light directions for each of a set of surface points in regard to the subject 12; of the light which enters the subject 12 from any incoming light direction from the set of incoming light directions, into any surface point A of the set of surface points, measuring a proportion of the light that exits out of the subject 12 in any outgoing light direction of the set of outgoing light directions from surface point B, where points A and B can be either a same point or different points.

The present invention pertains to an apparatus 10 for obtaining reflectance data of an object 7. The apparatus 10 comprises a diffuser 4 having a surface. The apparatus 10 comprises a mapping portion that effects a mapping between a light field at the object's 7 surface and a light field at the diffuser 4 surface for BRDF capture of the object 7.

Preferably, the mapping effected by the mapping portion is bi-directional. The mapping portion preferably includes a kaleidoscope 18 and a lenslet array 5 which forms an image of at least a portion of the object 7 surface on the diffuser 4 surface. Preferably, the kaleidoscope 18 has a top aperture with an area and the array 5 covers at least a portion of the area of the aperture. The apparatus 10 preferably includes a digital camera 22 that records the image on the diffuser 4.

Preferably, the apparatus 10 includes a light source 14 to illuminate at least a portion of the object 7 through the mapping portion. The lenslets of the lenslet array 5 are preferably placed sparsely so there are spaces between them through which light is sent into the kaleidoscope 18. Preferably, the kaleidoscope 18 is tapered.

The diffuser 4 is preferably non-back scattering. Preferably, the light source 14 is a pattern projector 28. The apparatus 10 preferably includes a beam splitter 26 portion in optical alignment between the camera 22 and the pattern projector 28. Preferably, the pattern projector 28 produces light and dark patterns onto the diffuser 4.

The light source 14 can be a polarized light source 14. The diffuser 4 is then preferably a non-polarization preserving diffuser 4. The apparatus 10 preferably includes a polarization patterned film disposed over the diffuser 4. The apparatus 10 is preferably handheld.

It should be noted that a 1:1 mapping exists (as opposed to a many to one mapping) which permits one to trace the light rays between incoming and emergent direction and a single spot on the diffuser 4 surface. An optional calibration step could be used to verify the mapping. A computer and algorithm may optionally be used downstream, but this may be separate as a past processing step.

The present invention pertains to an apparatus 10 for determining a plurality of values of a BRDF of an object 7. The apparatus 10 comprises a light source 14. The apparatus 10 comprises an image capture portion that captures reflectance data usable to determine a plurality of values of the BRDF in a single image capture.

The present invention pertains to a method for obtaining reflectance data usable to determine a plurality of values of the BRDF of an object 7. The method comprises the steps of illuminating the object 7. There is the step of effecting a mapping between a light field at the object's 7 surface and a light field at a diffuser 4 surface for BRDF capture of the object 7 with a mapping portion.

Preferably, the illuminating step includes the step of illuminating the object 7 with light passing through a kaleidoscope 18. The effecting step preferably includes the step of forming an image of the object 7 on an area of the diffuser 4 surface. Preferably, the effecting step includes a step of recording the image on the diffuser 4 surface with a digital camera 22 to capture a plurality of values of the BRDF of the object 7.

The illuminating step preferably includes the step of illuminating the object 7 with light passing through the kaleidoscope 18 and a lenslet array 5 which forms an image of at least a portion of the object 7 surface on the diffuser 4 surface. Preferably, the illuminating step includes the step of illuminating the object 7 with a pattern projector 28 that produces light and dark patterns onto the diffuser 4. The illuminating step preferably includes the step of illuminating the diffuser 4 with light passing through a polarization patterned film.

The present invention pertains to an apparatus 10 for measuring an 8D reflectance field of an object 7, or a 3D object 7. The apparatus 10 comprises a kaleidoscope 18 having an opening. The apparatus 10 comprises a projector 28 which illuminates at least a portion of the object 7 with a light passing through the kaleidoscope 18. The apparatus 10 comprises a plurality of cameras 22 dispersed in a staggered arrangement relative to the opening of the kaleidoscope 18 to take images of the surface of the object 7 through the kaleidoscope 18.

Preferably, the plurality of cameras 22 includes a first camera, a second camera, a third camera, and a fourth camera. The kaleidoscope 18 preferably has a plurality of mirrors, and wherein the first camera is placed over the center of the opening, pointing straight into the kaleidoscope 18 along a normal axis of the kaleidoscope 18, and the second and the third and the fourth cameras are tilted away from the normal axis of the kaleidoscope 18 and shifted in position halfway toward a mirror of the plurality of mirrors of the kaleidoscope 18. Preferably, the projector 28 sequentially illuminates different portions of the object's 7 surface.

The apparatus 10 preferably includes a computer in communication with the projector 28 and the cameras 22 to control the projector 28 and the cameras 22. Preferably, the projector 28 is a digital projector 28. The area of the surface of the object 7 is preferably divided into a grid by the computer and a plurality of portions of the grid are selectively illuminated by the projector 28. Preferably, each camera 22 takes an image of the portion of the grid when the portion is illuminated. The grid is preferably an 8×8 grid of 64 squares where each portion is a square of the grid, and the projector 28 selectively illuminates each of the 64 squares of the grid in turn. Preferably, the apparatus 10 includes a second projector 28 which illuminates the object 7 with light passing through the kaleidoscope 18. It should be noted there can be one camera 22 and a plurality of projectors 28 also used.

The present invention pertains to a method for measuring an 8D reflectance field of an object 7. The method comprising the steps of illuminating at least a portion of the object 7 with light from a projector 28 passing through a kaleidoscope 18 having an opening. There is the step of taking images of at least a portion of the surface of the object 7 through the kaleidoscope 18 with a plurality of cameras 22 dispersed in a staggered arrangement relative to an opening of the kaleidoscope 18. The cameras may be angularly staggered relative to the opening of the kaleidoscope.

Preferably, the illuminating step includes the step of illuminating sequentially with the projector 28 different portions of the object's 7 surface. The taking step preferably includes the step of taking with a first camera placed over the center of the opening, pointing straight into the kaleidoscope 18 along a normal axis of the kaleidoscope 18 an image of the object 7, and with the second and the third and the fourth cameras tilted away from the normal axis of the kaleidoscope 18 and shifted in position halfway toward a mirror of the plurality of mirrors of the kaleidoscope 18, respective images of the object 7.

Preferably, the illuminating step includes the step of illuminating selectively with by projector 28 a plurality of portions of a grid of the area of the surface of the object 7 which is divided into the grid by a computer in communication with the projector 28 and the cameras 22. The taking step preferably includes the step of taking with each camera 22 an image of the portion of the grid when the portion is illuminated. Preferably, the grid is an 8×8 grid of 64 squares where each portion is a square of the grid, and the illuminating step includes the step of illuminating with the projector 28 selectively each of the 64 squares of the grid in turn.

In each description above, the light source 14 may be replaced with ambient light.

In the operation of the invention, the apparatus 10 may be based on the principle of the kaleidoscope 18. BREWSTER, D. 1819. A Treatise on the Kaleidoscope, A. Constable, incorporated by reference herein. Generally used as a child's toy, a kaleidoscope 18 is a hollow tube of polygonal cross-section, whose inner walls are lined with front-surface mirrors. Peering into a kaleidoscope 18 creates an infinite "hall of mirrors" illusion; any surface sample placed at the far end will appear to "multiply" into many replicated images of itself.

Figure 1:
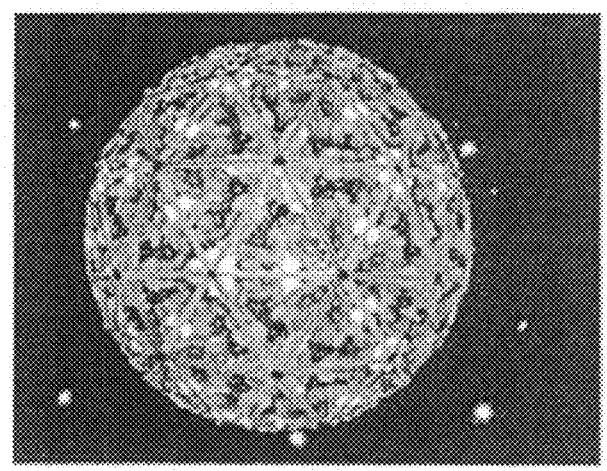
FIG. 1 is a view through a kaleidoscope.

A kaleidoscope 18 can be tapered, so that its far end is smaller than its near end. When this is done, the surface sample at the far end will look like a faceted virtual sphere. This is because each successive reflection reorients the reflected image of the surface a little further away from the perpendicular, until eventually the reflected images disappear over the horizon of the sphere [FIG. 1].

The effect is analogous to having an entire array 5 of cameras 22 all pointing toward the surface sample from different directions, which is precisely what is needed to measure the BTF. A single camera 22 pointed at a surface sample which is on the far end of a tapered kaleidoscope 18 will be able to see that same surface sample simultaneously from many different angles. These differently angled views of the surface sample appear to the camera 22 as different facets of the virtual sphere.

A nice benefit of this approach is that it can also be used as an illumination technique, using a light source 14 such as a single projector 28 to illuminate the same surface sample from many different directions. When a light source 14 such as a projector 28 is pointed down into the tapered kaleidoscope 18, different pixels of the projected image will arrive at the sample after having reflected off the kaleidoscope 18 walls in different ways, and therefore will approach the sample from various directions. In effect, different regions of the projected image behave like separate light sources 14. By keeping only selected pixels of the projected image bright, a particular direction from which to illuminate the sample can be chosen.

The optical paths of the camera 22 and projector 28 may need to be merged together, so that both can be pointed down into the kaleidoscope 18. This may be done through the use of a 45° beam splitter 26. Light from the projector 28 reflects off this beam splitter 26 down into the kaleidoscope 18. Light emerging back out of the kaleidoscope 18 may be transmitted through the beam splitter 26 and is then captured by the camera 22. This arrangement allows the projected image to be coaxial with the image seen by the camera 22. FIG. 2 shows an optical schematic of the device.

Measurement of the surface BTF proceeds by taking a sequence of successive sub-measurements, one after the other. During each submeasurement, preferably one region of the illumination image is bright, and all others are dark.

Because each region of the illumination image corresponds to a unique sequence of reflections of light off of the kaleidoscope 18 walls, that region will illuminate the surface sample from a unique sub-range of incoming light directions. A complete measurement consists of successive illumination of the sample surface by each of the illumination regions in turn. Alternatively, a partial measurement may be taken as well.

This approach has a number of advantages in comparison to previous methods for measuring the BTF. This approach requires no moving parts, allowing for full measurement to be performed very quickly. Since no physical movement is required between submeasurements, all submeasurements may be perfectly registered to one another. This property allows for a quite significant improvement in accuracy over previous approaches.

The apparatus 10 can be used to measure surfaces in situ, under any lighting conditions, without relocating the sample from its native setting. For some site-specific surfaces, such as living human skin, methods in current use for measuring BTF are simply not viable, since they all require isolating a sample into a light-controlled environment. Also, approaches that require the sample to be physically repositioned between measurements cannot be used to measure loose samples such as rice, dirt or pebbles.

This approach requires only a single CCD camera 22 or equivalent image capture device. This property allows the device to be fabricated at a low cost in comparison with previous methods that require multiple CCD cameras or equivalent image capture devices. This approach may richly sample the BTF. Even the first prototype of the present invention captured 484 illumination/view angle pairs, which exceeds the 205 pairs captured by the technique of Dana et al. DANA, K. J., GINNEKEN, B. VAN, NAYAR, S. K., AND KOENDERINK, J. J. 1999. Reflectance and Texture of Real World Surfaces. ACM Transactions on Graphics, 18, 1, 1-34, incorporated by reference herein. The technique is also versatile enough to allow the device to be portable and handheld.

All of these qualities make for a valuable new measurement tool, for use in situations for which current techniques are too bulky or unwieldy, or are simply impossible. For example, during a motion picture production, a member of the visual effects crew could use the apparatus 10 to measure the BTF of the skin of various parts of an actor's face, or the fabric of a costume or couch, or any prop or desk, wall, or floor surface of the set. With this information in hand, the appearance of these items can then be duplicated digitally with highly convincing realism and fidelity. Once the entire BTF has been captured, the filmmaker is free to make arbitrary decisions about lighting and camera 22 placement, which the virtual objects 7 can be synthesized to match.

The kaleidoscope 18 approach to BTF measurement is an extremely flexible one, with many design parameters to consider, depending on the objective.

Figure 3A:
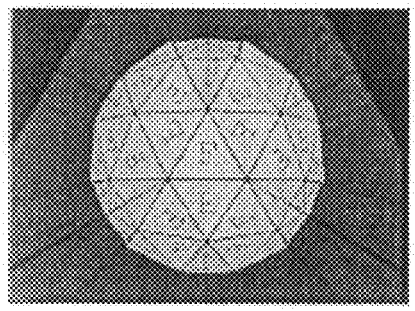
FIG. 3 shows kaleidoscope simulations for n={3,4,6}.
Figure 3B:
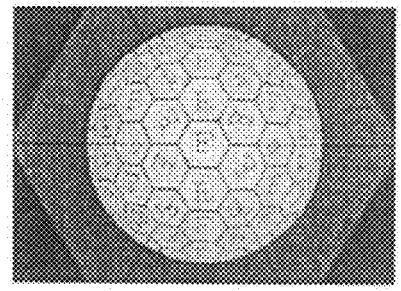
Figure 3C:
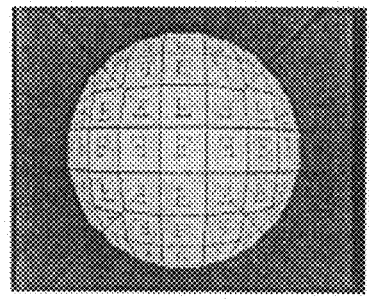

In general, the kaleidoscope 18 can be made as a regular polygon of n sides, for n>=3. A ray-tracer was implemented to better understand the effects of various values of n (see FIG. 3).

It is apparent that not every virtual facet is complete; many are fragmented, appearing to have real and virtual mirror seams slicing through them. For simplicity, only the unfragmented facets may be considered as usable data. In this case, the effect of n on fragmentation is a major factor in kaleidoscope 18 design, since the proportion of these facets varies with n. Alternatively, fragmented facets may be utilized as well.

Because the kaleidoscope 18 does not require any physical movement to make measurements, all objects 7 and surfaces will stay perfectly registered between subsequent measurements. This allows multiple scans to be made of an object 7 without any loss of precision. This can be exploited in various ways.

In particular, multispectral measurements of objects 7 that respond to different frequencies of light can be taken in useful or interesting ways. For example, objects 7 that refract light can be measured, such as crystals and glass, while varying the wavelength of the incoming light source 14. This will allow an accurate record to be taken of such multispectral phenomena as caustics. This record can subsequently be used by researchers in the field to construct synthetic models that accurately reproduce these phenomena.

A potential limitation of the kaleidoscope 18 is the step size in angular resolution. Each successive reflection increases angular divergence from the vertical axis by twice the tilt of the tube walls. For example, if the walls are slanted by 5 degrees from the vertical, then every bounce will increment this divergence by ten degrees. In this case, the kaleidoscope 18 can induce at most nine successive reflections, at which point this divergence reaches ninety degrees from the vertical—the theoretical limit. At this limit, light simply grazes the sampled object 7 from the side.

Greater angular resolution is desirable, but involves some tradeoffs. There are two distinct ways to increase angular resolution: (i) use a narrower taper angle to permit more bounces, and (ii) use multiple cameras and projectors within the kaleidoscope 18 aperture. As can be seen below, this presents the challenge of mounting and calibrating multiple cameras.

These two methods have complementary characteristics. The first method may decrease resolution, since the illumination source and imaging device may be required to cover more angular facets, and therefore can devote fewer pixels to each facet. On the other hand, this method is relatively simple and low cost to implement. The second method requires an increase in the number of projectors and cameras, increasing resolution at a cost of greater complexity and expense.

The image produced by a tapered kaleidoscope 18 consists of a discrete number of complete images of the subject 12 accompanied by a large number of fragmented images. As light is reflected multiple times, and becomes more divergent from the vertical axis, progressively more fragmentation may occur, and so the relative area of the fragmented data may increase. In previous work with the kaleidoscope 18 [HAN2003] only the complete images were used, and the fragmented regions were disgarded. This allowed for a very simple analysis of the data, but it wasteful in that much potentially useful data was disgarded:

Another way to look at the meaning of any given pixel of data captured through the kaleidoscope 18 is as a fragment in the four dimensional viewspace manifold $(u,v,\theta,\phi)$, where $(u,v)$ gives the location on a sample surface, and $(\theta,\phi)$ gives the solid angle direction from which the surface is being viewed. If the kaleidoscope 18 and the optics of the image capture device are fixed, then each pixel will always represent a particular small fragment of this manifold, having a fixed location and extent.

In order to get the most out of the data collected by the kaleidoscope 18, it is beneficial to determine the location and extent in the viewspace manifold of all visible pixel fragments, and then to piece these pixel fragments together to cover some portion of the manifold. In this piecing together process, it is beneficial to recognize pairwise relationships between pixels, including adjacency in the manifold, as well as overlaps and gaps. Where there are overlaps, it is beneficial to develop a fidelity metric, so that the pixel is chosen that best represents the data at that fragment of the manifold. Where there are gaps, it is beneficial to develop a reasonable technique to extrapolate into the missing region from available adjoining data, so as to approximately represent the surface in those missing regions.

The inverse of this map can be used to map between the pixels of the projected structured illumination source and the light that reaches the sample. When the two mappings (projection→sample and sample→camera) are concatenated, and error at each stage of mapping is properly measured and modeled, then an accurate transfer function is obtained in which the kaleidoscope 18 device acts as a functional filter.

The value of n also directly determines the shape of the base as the regular n-gon. However, image processing is most easily performed on rectangular images, so for any n=4, only the area of the largest inscribable square is utilized.

Triangular n=3 case was ultimately used, because of its simplicity in construction, and its highest proportion of whole unfragmented facets, though it does compromise on sample area and capture efficiency.

Varying the angle of taper also significantly affects what is seen through the kaleidoscope 18. Angle of taper refers to the amount that the kaleidoscope 18 narrows from one end to the other, and may be defined as the tilt angle between the mirrored side and the kaleidoscope's 18 optical axis.

A larger taper angle causes each successive reflection to tilt further away from the surface normal, which produces fewer facets that are visible before eventually disappearing over the horizon (elevation exceeds 90°). Conversely, a smaller angle of taper, forming a kaleidoscope 18 with walls that are more parallel, produces a greater number of visible facets with finer angular steps. However, capturing a greater number of facets in a single view may result in fewer pixels for each facet, and thus a reduction or relative reduction in spatial resolution.

Kaleidoscopes 18 with a relatively large angle of taper (and correspondingly fewer, larger facets) may be preferable to capture relief surfaces with high self-shadowing, such as pebbles, cloth, and jellybeans. This optimizes for greater spatial resolution within the sample; the tradeoff is fewer different angular directions. Tall slender kaleidoscopes 18 with a smaller angle of taper may be preferable (and correspondingly more numerous, smaller facets) to capture shiny surfaces with sharp specular peaks in reflectance. An optimal taper angle given a desired angular resolution, and desired final grazing angle can be calculated.

Figure 4:
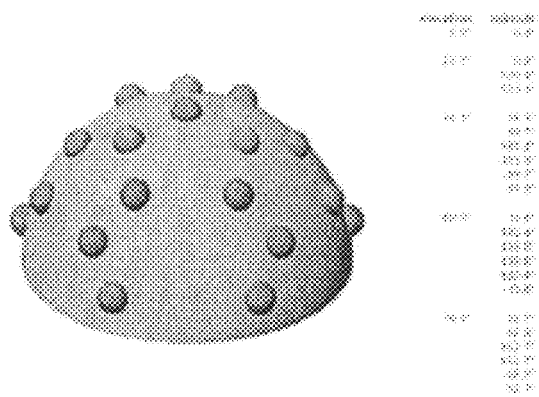
FIG. 4 shows the distribution of viewpoint and illumination angles.

In an exemplary embodiment, a taper that tilts from vertical angle by 9° was chosen. This provides 4 orders of reflections to the horizon, a final grazing facet elevation angle of 76°, and 22 complete views of the surface sample, providing $22^2$=484 distinct view/illumination angle pairs. See FIG. 4 for a tabulation of the actual angles of this exemplary embodiment, along with a visualization of those spherical coordinates on the unit hemisphere.

The remaining design parameter decisions include determining the scale of the kaleidoscope 18 that will best: (i) accommodate a surface sample of a desired size, and (ii) work with a given camera 22 field of view and projector 28 field of view without the use of any additional lenses or optics.

Before constructing the device, a simple OpenGL-based visualization tool to balance the various interrelated parameters was created. This allowed us to vary, in simulation, taper angle, base patch size, kaleidoscope 18 height, and field of view and distance of the camera 22 and the projector 28.

At this stage, it was realized that for a given sample size and tilt angle (a smaller angle produces a larger virtual sphere), the height of the kaleidoscope 18 (and therefore the bulk and expense of the front-surface mirrors) may be determined by the field of view of the camera 22 and projector 28: the kaleidoscope's 18 height can be reduced if a wider field of view is used. The camera 22 used had a vertical field of view of 39°; the projector 28 had a vertical field of view of 21°. The smaller of these (the projector 28) was the limiting factor, which ultimately determined the kaleidoscope's 18 height.

An exemplary kaleidoscope 18 has a triangular base edge length of 4", providing a maximally inscribed active sample area of 2.3" square, and has a total height of 14.7". The three trapezoidal front-surface mirrors needed for this design were cut for us from standard stock by a professional stained glass cutter.

For the beam splitter 26, an ordinary plate of glass may be used, which may have approximately 96% transmission at a 45° incident angle. Because the projector 28 may have a high luminance, this glass may reflect more than sufficient illumination down into the kaleidoscope 18.

LCD projectors were generally found to be unsuitable for purposes here, because the reflectivity of the beam splitter 26 varied with polarization. For this reason, experiments were conducted with a DLP projector, which provides unpolarized illuminance. The camera was a Canon PowerShot G1, which has a capture resolution of 2048×1536. A small aperture was maintained so as to maximize depth of focus.

In this exemplary embodiment, a large proportion of light may be transmitted through the beam splitter 26, and end up being projected onto the wall of the laboratory. Some of this reflected light may make its way back to the beam splitter 26, and a small portion of that light may be reflected up into the camera 22. A matte black surface may be placed on the wall, which may absorbed almost all of this unwanted light. The color calibration step may compensate for what little was left.

Figure 5:
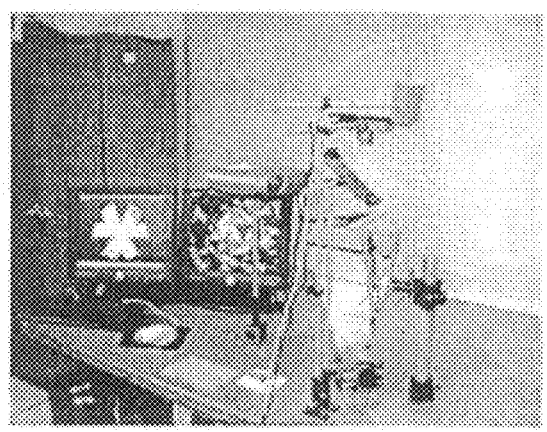
FIG. 5 shows the experimental setup for the apparatus.

To maintain precision, it is preferable to not jar the kaleidoscope 18. For this reason, the entire apparatus 10 may be installed on an optical table. A sample to be measured may be first slid underneath the kaleidoscope 18, for example upon a mechanical stage. The stage may be then elevated until the sample is flush with the kaleidoscope 18 opening. The laboratory setup is shown in FIG. 5.

Deviations in brightness and color balance may come from many sources, including mirror coatings, mirror absorption, and mismatch between the projector 28 "white" color and the camera 22 "white" color. In the measurements dichroic mirror coatings caused slight color shifts at different incident angles, which showed up as variations in hue between different facets of the virtual sphere.

There may be a dropoff per unit sample area at the outer facets, which may simply be due to the fact that a tilted facet presents fewer pixels to the projector 28. It may be found that both spatial resolution and brightness drop off at the most extreme angles.

To compensate for such deviations, as well as others not accounted for, the device may be calibrated in situ using for example a Kodak standard color chart. This calibration may be only done once, since the projector 28, camera 22, beam splitter 26 and mirrors may all remained unchanged. Over a long time frame, it may be wise to periodically recalibrate to account for gradual shifts in the projector 28 lamp as it ages.

Image processing may be used to identify and extract the many reflected images of the surface sample. This procedure may need to be performed only once, using the following exemplary in situ calibration:

A test pattern, for example a planar 3×3 checkerboard may be placed under the kaleidoscope 18 and corner detection performed to identify the sub-pixel coordinates of each reflected checkerboard image. Those points may be used to compute the best homography transform that maps each patch to the unit square.

Those transformations may be in turn applied to each of the illumination imaging shots. In an exemplary embodiment, there are 22 illumination imaging shots and the resulting 22 square sub-images may each be clipped out, and saved to disk. The result in this exemplary embodiment was a 22×22 array 5 of images indexed by projector 28 facet and camera 22 facet. Correction for the lens distortion of the camera 22 is preferably done only once, for example using the technique of Zhang. ZHANG, Z. 1999. Flexible Camera Calibration By Viewing a Plane From Unknown Orientations. International Conference on Computer Vision (ICCV '99), Corfu, Greece, pages 666-673, September 1999, incorporated by reference herein.

It is preferable to determine which pixels in the projected image illuminated each kaleidoscopically reflected image of the surface sample. This may be done manually and may include implementing a triangle editor in software. Using the actual image from a video camera 22 peering into the kaleidoscope 18 as a guide, this editor may allow a user to quickly outline each of the 22 triangles.

Preferably, this step may be done automatically as follows: The projector 28 would project a known tracking pattern, which the camera 22 would record. This data would then be used to recover, in a single step, the projection matrix of the projector 28 itself, as well as all the projection matrices of all the reflected images of the surface sample. This calibration also would need to be performed only once.

Figure 6A:
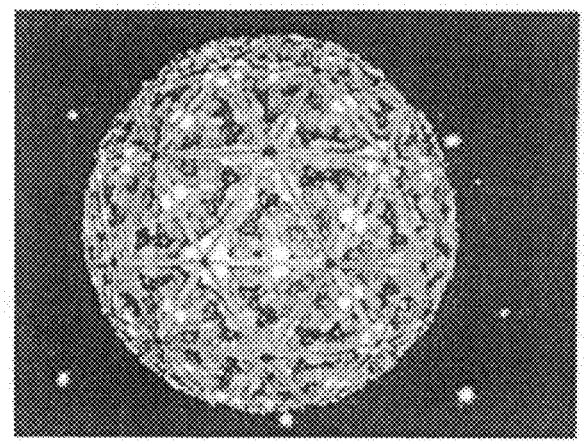
FIG. 6 shows two multi-view captures of "jellybeans", under different illumination directions.
Figure 6B:
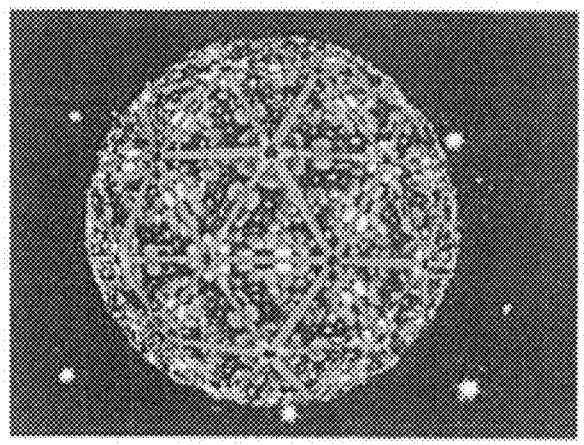
Figure 9:
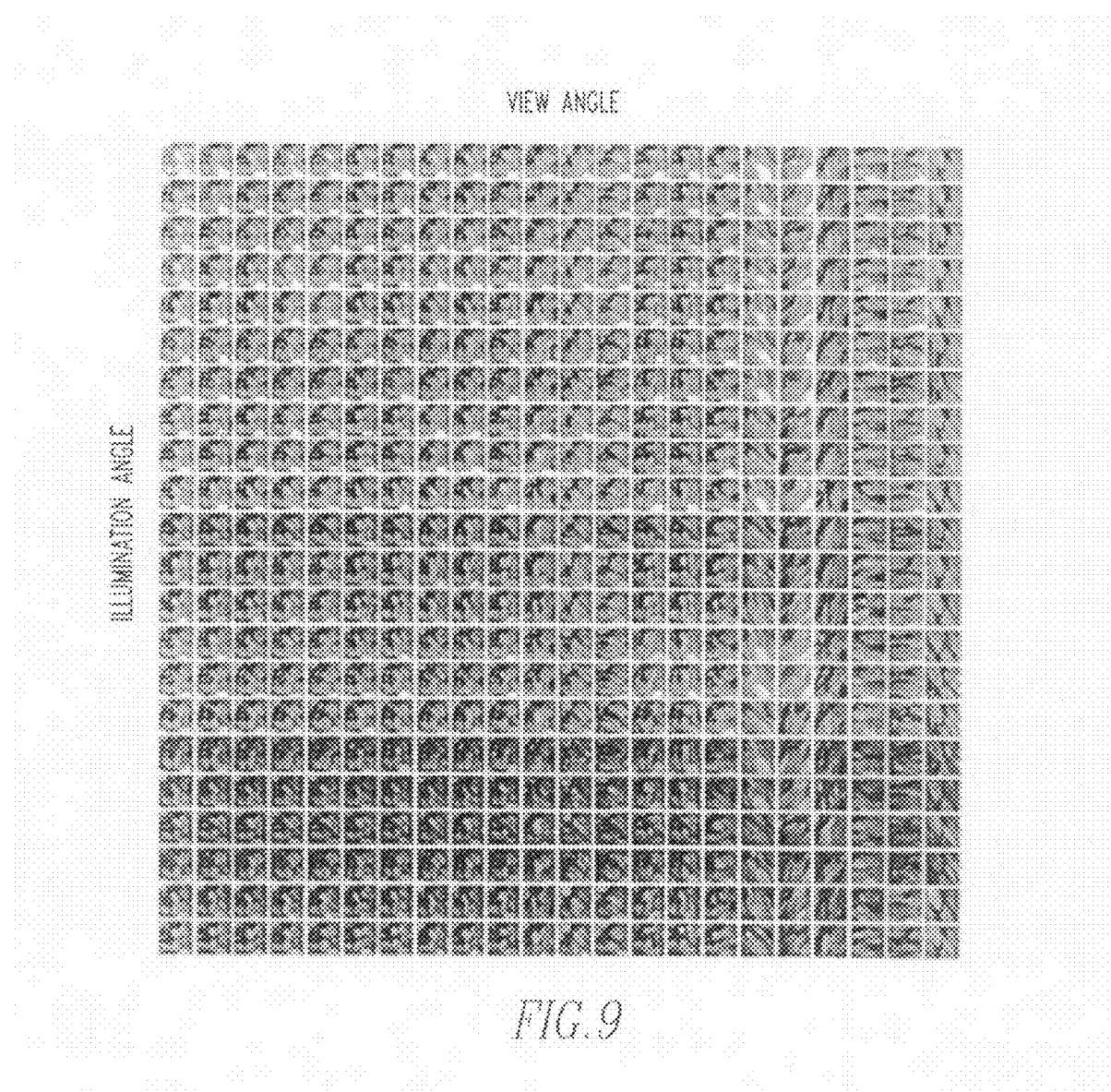
FIG. 9 shows the full 22×22 image BTF measurement of "jellybeans".

FIG. 6 shows two multi-view image captures of a sample of jellybeans, taken with two different illumination angles, and FIG. 9 shows the full, structured 484 image BTF after sub-image extraction has been performed.

Figure 7:
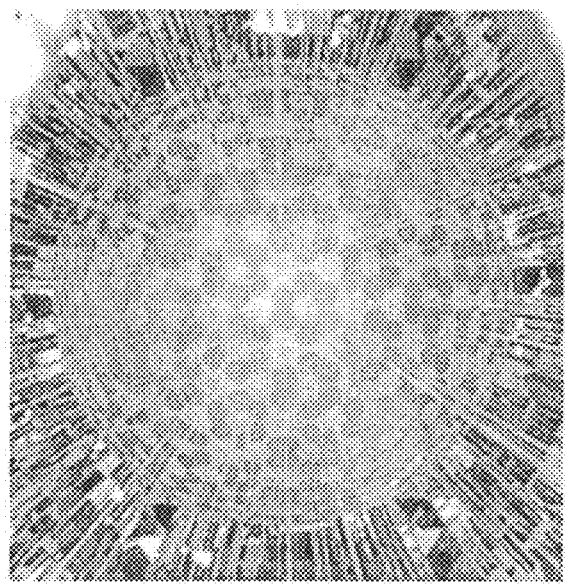
FIG. 7 shows a multi-view image of a penny, using a longer taper kaleidoscope.

FIG. 7 shows a multi-view image of a coin captured with an exemplary kaleidoscope 18 having a relatively small taper. This device has 79 unfragmented facets, and can capture $79^2=6241$ distinct view/illumination angle pairs. A small-taper kaleidoscope 18 may be particularly useful for measuring fine variations in reflectance due to small differences in angle.

For surfaces which have appreciable sub-surface scattering, it is useful to measure the BSSRDF (Bidirectional Scattering Surface Reflectance Distribution Function) of the surface, preferably by illuminating only a small spot of the surface sample, and then to measure the light which emerges from locations within the larger region that surrounds this spot. JENSEN, H. W., MARSCHNER, S. R., LEVOY, M., AND HANRAHAN, P. 2001. A Practical Model for Subsurface Light Transport. In Proceedings of ACM SIGGRAPH 2001, ACM Press/ACM SIGGRAPH, New York. E. Fiume, Ed., Computer Graphics Proceedings, Annual Conference Series, ACM, 511-518, incorporated by reference herein. By incrementally moving this illuminated spot and taking associated measurements at each successive spot position, what can be termed the sample's BSSTF (Bidirectional Scattering Surface Texture Function) can be measured:

$$BSSTF(u_i,v_i,u_e,v_e,\theta_i,\phi_i,\theta_e,\phi_e)$$

The BSSTF, may also be described as the reflectance field in [Debevec et al. 2001], any may be an eight dimensional function: two for the entry point of the light into the sample, two for the exit point of the light out of the sample, two for incoming spherical angle, and two for outgoing spherical angle. Because this technique requires no physical movement, it is now feasible to accumulate the many measurements needed to build this eight dimensional function in a timely manner without any loss of precision from mechanical movement.

Figure 8A:
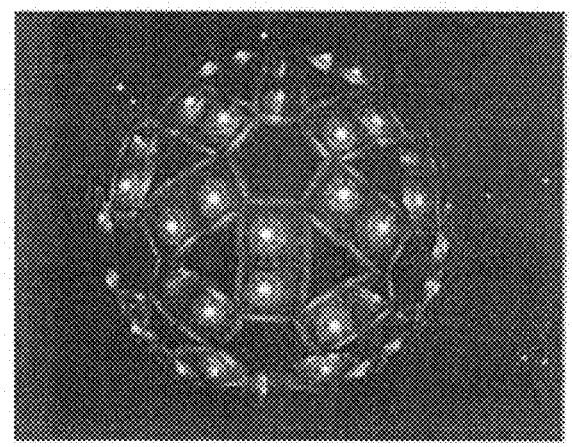
FIG. 8 shows two measurements of a BSSTF.
Figure 8B:
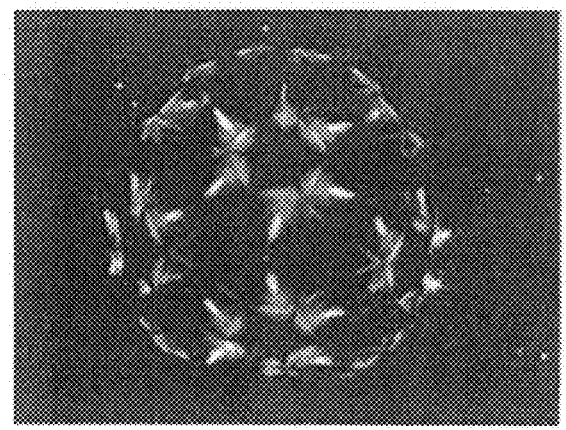

BSSTFs have been measured through the primary kaleidoscope 18. FIGS. 8*a* and 9*b* show two sub-steps of a measurement of a translucent block, in these early tests illuminated by a laser. Analogously, the projector 28 may scan an image of a fine spot across the surface sample area.

High dynamic range (HDR) capture capability can be accomplished, by taking multiple image captures of varying exposure lengths, as in Devebec and Malik. DEBEVEC, P. E., MALIK, J. 1997. Recovering High Dynamic Range Radiance Maps from Photographs. In Proceedings of ACM SIGGRAPH 1997, ACM Press/ACM SIGGRAPH, New York. Computer Graphics Proceedings, Annual Conference Series, ACM, 369-378, incorporated by reference herein.

The most generally useful embodiment of the technique may be a small apparatus 10, which may be hand held, and which may be battery operated, and which may be used in situ to measure surface reflectance in somewhat the way a light meter is currently used to measure illuminance. The apparatus 10 may be held against any surface sample to be captured. A preferable component change may be a replacement of the projector 28 by a set of small individually collimated white light LEDs or other suitable light source 14. Because the apparatus 10 may lie flush against the sample, unwanted ambient light could be excluded from the measurement through the use of a light curtain. This may allow the measurement to be made under uncontrolled lighting conditions. In this embodiment, the technique may have the greatest ability to positively impact the motion picture industry, by helping to reduce costs and increase flexibility for digital set construction and digital actor replacement.

At the other end of the scale, a large (for example room-scale) version of the apparatus 10 can be implemented. In an exemplary embodiment of this arrangement, each wall of a high-ceiling room may be a mirror (e.g. trapezoidal). A two dimensional array 5 of downward-pointing cameras and projectors may be mounted on or near the ceiling. This apparatus 10 may provide a relatively economic way to simultaneously capture a live performance and may handle a large number of camera 22 angles which may be under controllable lighting conditions.

The kaleidoscope 18 may be used to do area BTF capture, which may be a far more demanding task than single point BRDF capture. This means that for BRDF capture there may be pixels to burn in the digital camera. The right information just needs to be directed to these pixels.

In the discussion that follows, it is assumed that this sample is relatively homogeneous, its surface points have some degree of interchangeability.

In particular, it may be desired to perform a capture that may be dense in emergent angular directions (on the order of 500 samples upon the angular hemisphere), but which may be sparse in illuminating angular directions (such as the 7 illuminating angular directions provided by Integra).

To effect this density, the following is done:

On the top (wider) end of the kaleidoscope 18, place a lens array 5. This lens array 5 will preferably completely span the area of the top kaleidoscope 18 aperture. The lenslets may be placed sparsely, because the structured light source 14 may be using the space between them to send light down into the kaleidoscope 18.

Each lenslet may focus its image of the object 7 at the base of the kaleidoscope 18 up onto a transmissive optical diffusor screen 24 which may be placed a short distance above the lenslet array 5. The digital camera 22 may be placed above the apparatus 10, from where it may record the image formed upon this optical diffusor screen 24. It is preferable that this optical diffuser 4 be non-back-scattering. For example, holographic diffusers 4 can have extremely low back-scatter.

From the point of view of the object 7 at the base of the kaleidoscope 18, there may be a dense array 5 of lenslets over the entire visible hemisphere above the object 7. In this apparent dense array 5, each actual lenslet may be represented multiple times, once in its original position, as well as multiple additional times as it its image is reflected through the kaleidoscope 18.

The apparatus 10 as described so far may not fully utilize the resolution of a digital camera 22. Assume that the object 7 at the base of the kaleidoscope 18 consists of a single bright point of light. Even at a one degree angular spacing between successive lenslets, there will be only several thousand points of light formed upon the diffusion screen 24 for the camera 22 to resolve. Even given that these points are not uniformly distributed upon the optical diffuser 4 screen 24, the resulting reflectance pattern may still greatly underutilizes the high resolution of a modern digital camera 22.

Since an object 7 being measured may actually form an area, not a single point may be made use of. The structured light source 14 may be used to illuminate the object 7 in such a way that the light which reaches different points of the object 7 may approach the object 7 from different directions. This may be done by directing light toward different points on the object 7 surface by way of different reflection paths in the kaleidoscope 18. In this way, different illuminated points on the object 7 may receive light that arrives from differing angular directions.

The key concept:

The combination of kaleidoscope 18 and lenslet array 5 may effect a mapping between a light field at the object 7 surface and a light field at the diffuser 4 surface. This mapping may be bi-directional.

The light field of incoming light direction can vary, onto the object 7 by varying the projected image which forms the pattern of light. The illumination can also be effected by a fixed projection image pattern, in which case no computer control is required for illuminance. The pattern projector 28 can be placed either side by side with the camera 22 or else merged through a beam splitter 26. In either case, the light from the pattern projector 28 may be focused, preferably in structured light/dark patterns upon the non-back-scattering optical diffuser 4 screen 24. From there, it may go down through the lenslets and into the kaleidoscope 18, and may form the desired illuminance light field as in the previous paragraph. Note that because the projection pattern may be fixed, a relatively high resolution pattern can be effected inexpensively.

Note also that with this arrangement the BRDF can be gathered in a single image capture. This is an enormous improvement over other techniques which apparently require several minutes per BRDF capture.

Figure 10:
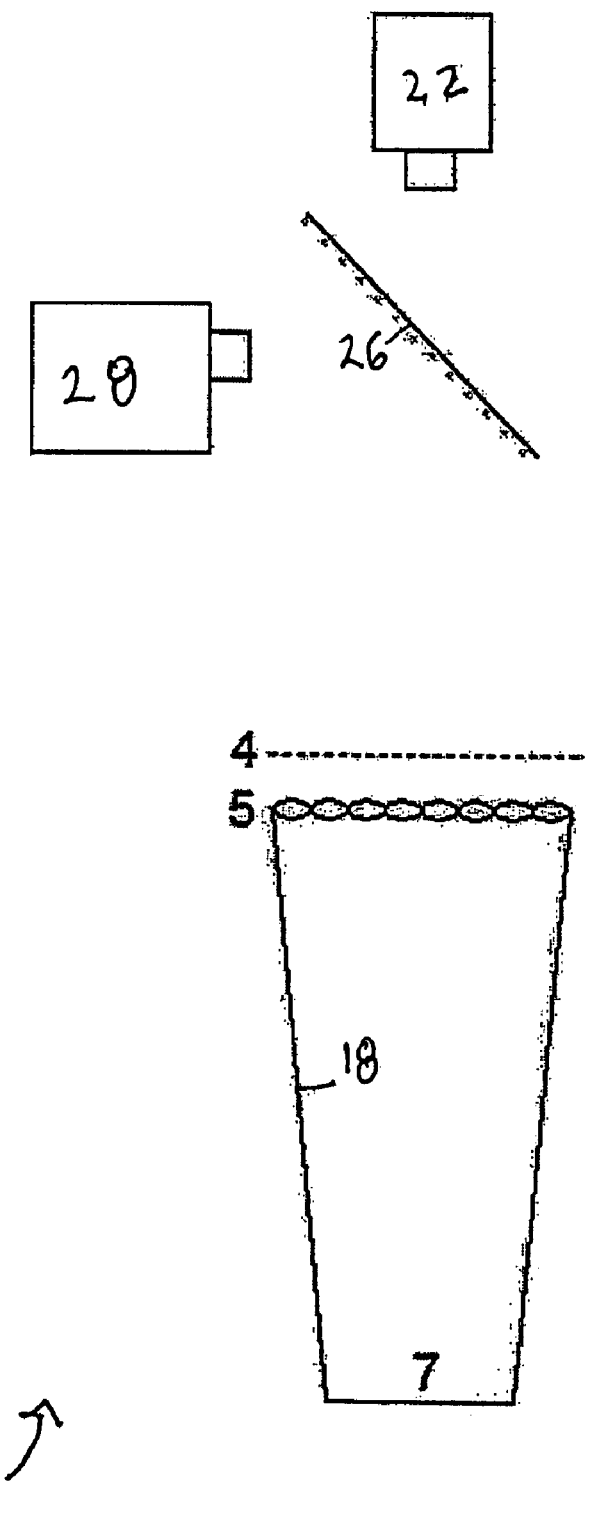
FIG. 10 shows the components of another embodiment of the present invention.

FIG. 10 shows the preferable optical components.
1. Digital camera 22
2. Pattern projector 28
3. Beam-splitter 3
4. Non-backscattering diffuser 4
5. Lenslet array 5
6. Tapered kaleidoscope 18
7. Object 7 to be measured In a slightly different simpler embodiment, the pattern projector 28 can be gotten rid of altogether. Instead, a film may be placed on top of the optical diffuser 4 surface which may contain a pattern of alternately polarized regions. One description of how to make such a film is given in the 1995 U.S. Pat. No. 5,398,131 granted to Hall and Johnson, incorporated by reference herein. When a polarized light shines down through this film, only light from those regions with the proper polarization may pass through the film, down onto the optical diffuser 4 screen 24, then down onto the lenslet array 5, and finally down into the kaleidoscope 18 tube. An alternating polarization pattern may be used such that when passed through the optical system of lenslet array 5 and kaleidoscope 18 tube, may form the desired illuminance light field at the base of the kaleidoscope 18.

In this embodiment, an optical diffuser 4 may be used which does not preserve polarization. This may ensure that there will be no effect from the polarization patterned film upon the image that will be captured by the camera 22 of light returning up through the kaleidoscope 18 tube.

Figure 11:
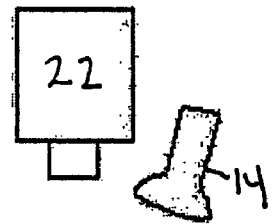
FIG. 11 shows yet another component of another embodiment of the present invention.
Figure 11:
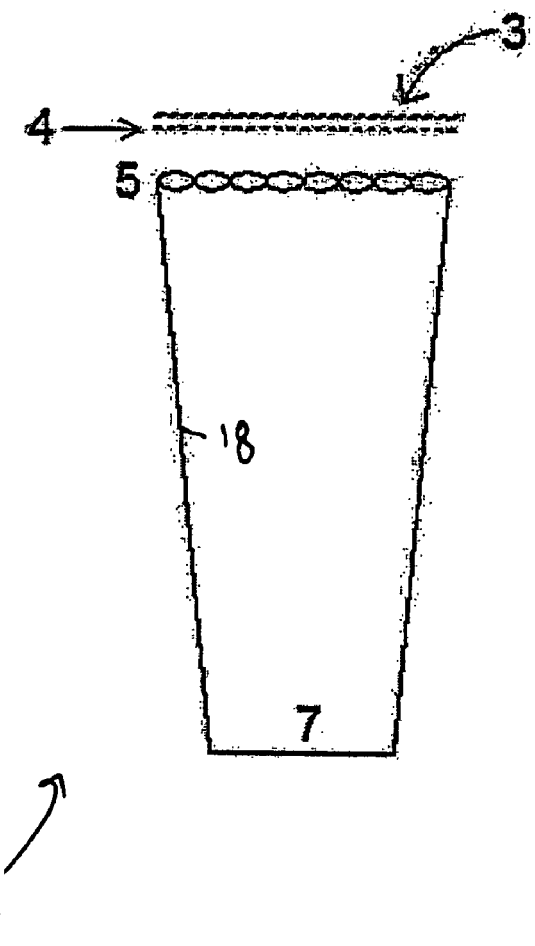

Also, in this embodiment a beam-splitter or a pattern projector 28 is not needed. Instead, an unstructured polarized light source 14 may be employed which is preferably next to the camera 22. Removing the need for a beam-splitter and projector 28 may make it far more practical to create a small hand-held BRDF measurement device. The optical components are shown in FIG. 11.

In the operation of the invention, a novel technique of using a kaleidoscope 18 to measure surface reflectance was introduced by [Han and Perlin 2003]. The current work extends that technique. In an exemplary embodiment a tapered triangular kaleidoscope 18 is used whose design provides 22 angular samples about the hemisphere for both illumination and view ($22 \times 22 = 484$ samples in total). A light source 14, such as a projector 28, sends a sequence of patterns of illumination into the kaleidoscope 18 through a beam splitter 26, as first described by [Han and Perlin 2003].

Figure 12:
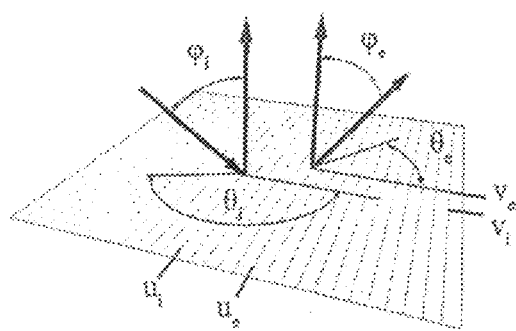
FIG. 12 shows the 8 dimensions of the Reflectance Field $R(u_i,v_i,\theta_i,\phi_i,u_e,v_e,\theta_e,\phi_e)$.

FIG. 12 shows the 8 dimensions of the Reflectance Field $R(u_i, v_i, \theta_i, \phi_i, u_e, v_e, \theta_e, \phi_e)$.

Figure 13:
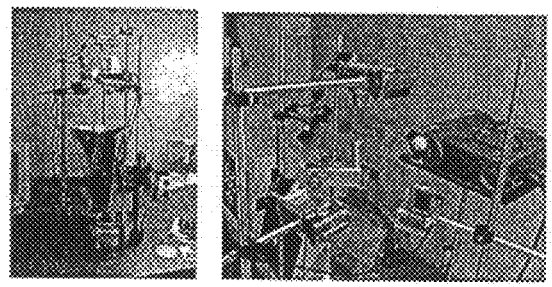
FIG. 13 shows a multi-camera kaleidoscope lab setup.

It may be desired to increase the sampling in the angular dimensions, for illumination and/or view (light incidence and existence). This may be addressed by utilizing multiple cameras 22. The multiple cameras 22 may be staggered. They may be placed in an angularly staggered arrangement (FIG. 13). The angularly staggered arrangement may include a tilt relative to a reference plane (such as the opening of the kaleidoscope). Alternatively, they may be positionally staggered relative to a reference camera 22 or to the opening of the kaleidoscope 18. A positionally staggered arrangement may include placing a plurality of cameras at points that are translated relative to a reference camera and/or a reference plane (such as the opening of the kaleidoscope). In place of the single camera of Han and Perlin [2001], a plurality of cameras, for example four cameras in an exemplary embodiment, may be placed over the mouth of the kaleidoscope 18. One camera may be placed in the center, pointing straight downward. Each of the other three cameras may be tilted, for example away from the normal axis, and may be shifted in position, for example half-way toward one mirror of the kaleidoscope 18. The result may be a four-fold increase in the angular resolution of the device (FIG. 14).

Angular density may be increased, as suggested in the original kaleidoscope 18 paper, by using a narrower taper angle to create more reflections of the primary surface patch. However, this may require a four-fold increase in camera 22 resolution to maintain the same spatial sampling resolution. The approach here exploits the economic "sweet spot" of commodity consumer level digital cameras (currently about $300 for a 3-5 Megapixel camera). To put this in perspective, a 14 Megapixel digital camera currently costs about $5000— about 17 times the cost of a commodity digital camera. Even as camera prices and pixel counts continue to change over time, an architecture that can make use of commodity components may be advantageous.

Figure 14:
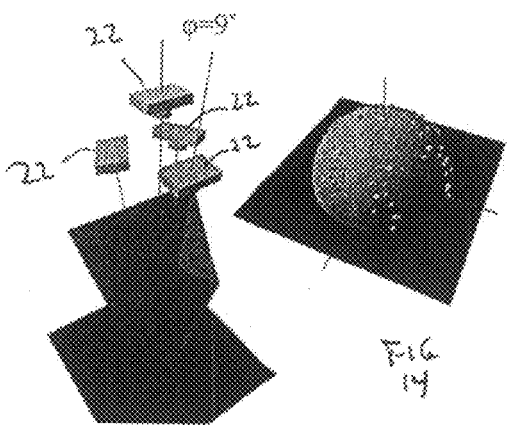
FIG. 14 shows a multiple-camera physical setup and the resulting angular distribution.

It is important to note that the resulting viewing directions (e.g. 88 in the exemplary embodiment) may not, relatively speaking, be uniformly distributed about the hemisphere—they may be clustered around the directions captured by the kaleidoscope 18 (e.g. 22 directions in the exemplary embodiment, refer FIG. 14).

Similarly, multiple projectors 28 may be staggered in an analogous manner and may increase angular resolution in the illumination dimension. Angular separation between exitant images (camera) may be much more critical to rendering quality than angular separation between illuminance images (projector 28), so there may be no compelling reason to use multiple projectors 28. If multiple projectors 28 are used, they may be staggered angularly or positionally. Thus a plurality of projectors may be arranged with some relative tilt to a reference projector or reference plane (such as the opening of the kaleidoscope). Also a plurality of projectors may be arranged at positions which are translated relative to a reference projector and/or reference plane (such as the opening of the kaleidoscope).

Figure 16:
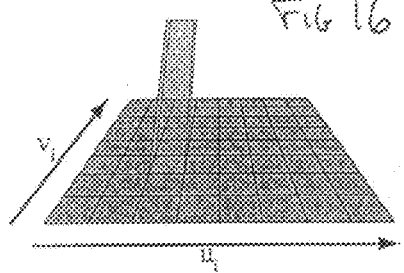
FIG. 16 shows spatially-varying illumination technique—the projector scans a spot of light across the sample surface.

To measure the full 8D reflectance field, the kaleidoscope 18 BTF acquisition technique may be enhanced by utilizing a light source 14 such as a digital projector 28 to sequentially illuminate different portions of the target surface: Rather than take a single measurement of the patch being uniformly lit from a particular lighting direction, the sample area may be subdivided, for example into a uniform 8×8 grid, and selectively illuminate each of the 64 squares of this grid in turn. This scan sequence may be repeated for each facet in the virtual illuminance sampling sphere (FIG. 16). Various subdivisions other than an 8×8 grid may be used.

The use of a scanning projector 28 may be similar to [Masselus 2003]. Masselus achieves a faster scan rate by scanning four (widely separated) regions in parallel.

An AR-treated beamsplitter may be used in place of the beamsplitter and may be made of standard plate glass used in Han and Perlin [2003]. The double reflection which may be caused by untreated glass may result in ghosting artifacts in the projection of small features. The ability to project small features without any ghosting may be crucial to the accuracy of the spatially varying illumination process.

Figure 15:
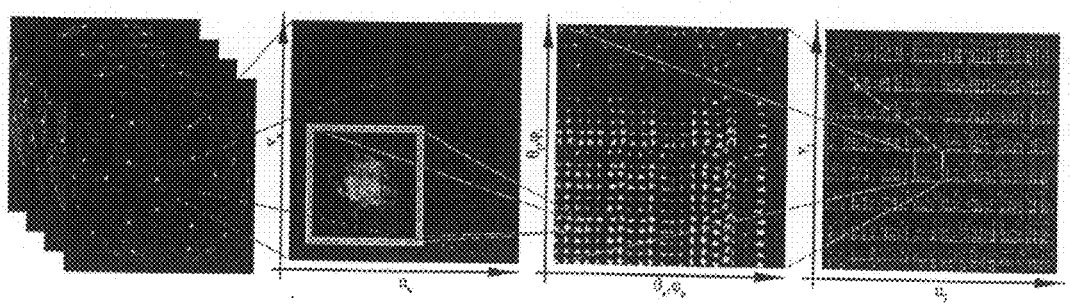
FIG. 15 shows raw camera image data extraction, tabulation, and organization.

FIG. 15 shows raw camera 22 image data extraction, tabulation, and organization.

Figure 18:
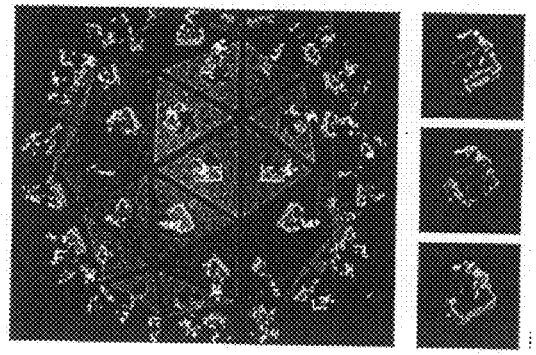
FIG. 18 shows raw image capture of a 3D mode and three samples under different illumination conditions in the panels on the right.

In addition to measuring the reflectance of flat surfaces with appreciable variation in depth, the technique of Han and Perlin [2003] can be extended to capture the appearance of many fully 3D models. Due to the irregular distribution of facet reflections in a triangular kaleidoscope 18, successive reflections of an object 7 may be visually staggered. Because of this property, when a small object 7 which is taller than it is wide is placed into the kaleidoscope 18, all views of the object 7 (e.g. 22 views in an exemplary embodiment) can be seen (FIG. 18).

Segmentation of the raw captured data into separate views may be more difficult in this application than in the case of simple planar rectification, since the object 7 is preferably separated out from partial reflection fragments behind it. This separation may be accomplished by manual rotoscoping. This may involve masking and may need to be done only once per camera 22 for a given object 7. The same mask can then be used for all lighting measurements.

Reflectance measurements may be performed in high dynamic range precision, for example by taking multiple exposures [Debevec and Malik 1997].

Exposure times may range from 2000 ms to 8 ms. HDR may be used to capture many of the subtle effects related to spatially varying illumination conditions, such as subsurface scattering.

The projector 28 utilized for illumination in an exemplare embodiment is based on a singlechip DLP, a technology that may provide gray-scale reproduction via fine-grain temporal multiplexing, and color reproduction by coarse-grain temporal multiplexing (via a color wheel) of the three color primaries. This multiplexing can potentially interfere with the opening and closing of the camera 22 shutter, and thereby cause a bias in measurement. Since the light source 14 may only need to be white, the color-wheel from the projector 28 system's optical path may be removed and set the framebuffer color to either pure black or white for all pixels. At these settings, the DLP may not do any temporal multiplexing, so there may be no time-varying flicker that could interfere with the opening and closing of the camera 22 shutter.

Figure 17:
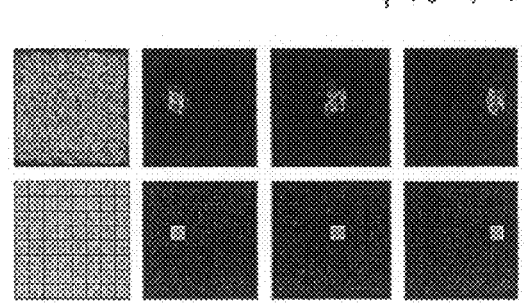
FIG. 17 shows a top sample surface illuminated by projector spot pattern and a bottom projection pattern.

FIG. 17 shows a top sample surface illuminated by projector 28 spot pattern and a bottom projection pattern.

The exemplary setup acquires the Reflectance Field with a sampling of 8×8 for the incident illumination positions $(u_i, v_i)$, 22 incident illumination angles $(\theta_i, \phi_i)$, 22×4=88 exitant viewing angles $(\theta_e, \phi_e)$, and up to 200×200 texture surface samples $(u_e, v_e)$. A complete acquisition session, through the 4 cameras, each using 4 exposures for each sample, takes 22,528 individual photos, with the raw dataset being about 45 GB in size, and taking over 4 days to complete. The USB camera-computer data transfer interface may be a primary bottleneck.

For most materials, the light that enters the material may be reflected and/or reemitted after subsurface scattering in an area that may be very local to the incident location. In other words, subsurface scattering may be a mostly local phenomenon. Because of this property, data size may be reduced considerably, for example by cropping the sample by one-half the sample length in both dimensions of the sample image. This cropping may yield a significant reduction in data size (in the exemplary embodiment this may yield a 4:1 reduction in data size).

For image processing it may be convenient to rectify and store every image dataset in memory in an axis-aligned rectangular format. However, for image synthesis purposes, where the image data may be applied as a texture and may need to undergo projective transformations in the process of rendering, it may be equally convenient to store the images directly unrectified, while also storing the planar homography transform so that the image data can later be transformed in the rendering pipeline.

Thought of another way, it may be a waste of texture memory to expand a grazing-angle view of a surface to full size resolution when there is no actual information being added to the representation. However, packing non-rectangular subimages into a system's rectangular memory structure may also be inconvenient. The solution may be to modify this technique by partially rectifying the image to permit better packing densities. This partial rectification may avoid expanding the stored image sample in the direction of foreshortening. The resulting packed samples may require only 65% of the original space.

Figure 19:
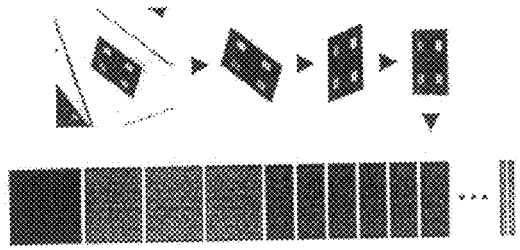
FIG. 19 shows packing of partially-rectified images in texture memory.

FIG. 19 shows an exemplary packing of partially-rectified images in texture memory.

Once a sampling of the reflectance field has been acquired, the appearance of the surface or model can be reconstructed under novel spatially-varying illumination conditions and novel view directions.

For a dense sampling, with no other data modeling, interpolation (e.g. linear interpolation) may be used to achieve the best signal reconstruction, and so reconstruction can be considered a compression problem that allows the nearest neighbor samples to be accessed dynamically on demand. A number of common implementation optimization techniques may be used, such as texture compression and/or intelligent texture tile caching to manage the dataset size and make it available for fast lookup.

The surface can be relit by directly summing the individual basis images for each of the $u_i, v_i$ incident illumination directions positions and incident lighting directions (e.g. 22×8×8 in an exemplary embodiment), and may weight each one for example by the corresponding radiance value in the desired lighting environments' 4D incident light field.

User-friendly synthesis of the lighting environment using more familiar devices such as ambient, directional, and spot light sources 14 may be handled by dynamically filtering and converting each synthetic illumination pattern into the corresponding light field coefficients.

When the incident light field is sparse (e.g. a limited number of directional spotlights illuminate the surface), a pixel shader may be used that works with single arbitrary light directions. For an arbitrary lighting vector it may be desired to quickly compute the 3 nearest points in a Delaunay triangulation of the acquired illumination directions. These points may be stored and their associated barycentric weights in the RGB components of two cubemaps. This may be done on a multipass basis into an accumulation buffer in floating-point precision for each non-zero light direction and position.

A different pixel shader may be used to relight the surface with a fully dense incident light field, which may be more optimized for accessing all lighting directions at each pixel (e.g. 22 in the exemplary embodiment). The lighting environment is filtered and prepared as an RGB texture to this shader (for, example a 22×8×8 RGB texture in the exemplary embodiment).

Figure 20A:
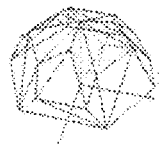
FIG. 20a shows a delaunay triangulation on the hemisphere of the 22 illumination directions.
Figure 20B:
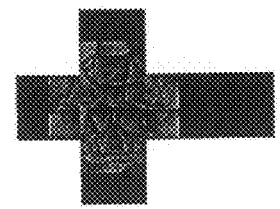
FIG. 20b shows precomputed cubemap texture of barycentric weights.

FIG. 20a shows a delaunay triangulation on the hemisphere of the 22 illumination directions. FIG. 20b shows precomputed cubemap texture of barycentric weights.

In reconstructing a view of the surface, the denser sampling of viewpoint directions may be obtained by utilizing the multiple staggered camera 22 approach may permit us to use barycentric interpolation here as well. This 3-sample lookup and weighted average may be done for each lighting condition as well so that for instance the case of a single directional light source 14 requires 3×3=9 texture lookups.

Figure 21:
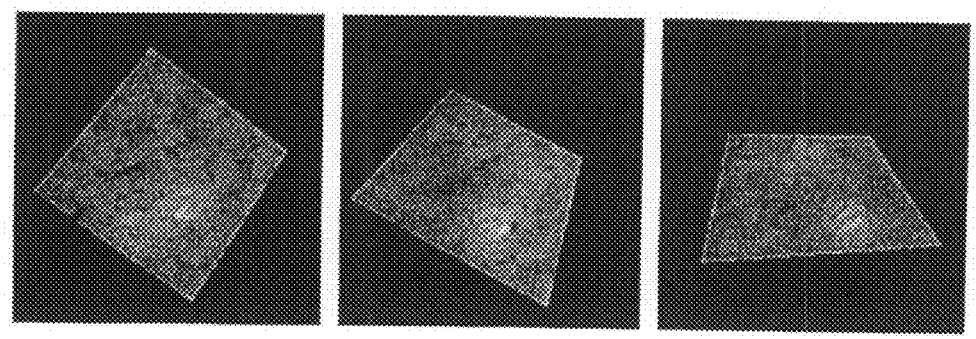
FIG. 21 shows several frames from a real-time animation running on the GPU; three spotlights moving in position and direction illuminate a sampled patch of rice, while the viewing direction rotates.

FIG. 21 shows several frames from a real-time animation running on the GPU; three spotlights moving in position and direction illuminate a sampled patch of rice, while the viewing direction rotates.

In an exemplary embodiment on an nVidia GeForce FX 3000 graphics card running at a core/memory speed of 450/950 MHz, views were reconstructed of the surface at interactive rates (100 fps+) for a sparse set of spotlights freely moving about the surface. To do arbitrary lighting with the complete 8×8×22 incident light field 64 successive shader passes are done, declaring 22 lights per pass, and achieve a modest 4 fps.

It should be noted that the arrangement for multiple projectors is exactly analogous as that for multiple cameras. Again, staggering both in position and/or angle can be used, with specific examples including halfway towards the faces of the mirror, or halfway towards the vertices of the kaleidoscope.

The apparatus 10 can also be used on 3D objects 7. After raw image capture the images may be post-processed either by manual/human processing or via automated or semi-automated methods. When the apparatus 10 is used on objects 7 with significant depth or 3d shape it may be more likely that part of the hull (tile is no longer applied for 3D objects 7, since their reflective data is not a simple tile anymore—they have silhouettes or "hulls") does not contain the object 7 of interest or the object 7 of interest may extend "beyond" the simple "tile" bounds found with a flat object 7, in a shape-dependent way (e.g. it may contain in part an image of a kaleidoscope 18 platform or background of the object 7 and is not of interest). This is in contrast to relatively flat or flat objects 7 of sufficient size which may fill each hull and where this step may not be needed. So in such cases where post-processing is desired the task is analogous to a classic image segmentation task, i.e. to at least in part separate "foreground" and "background" where "foreground" includes the object 7 of interest and "background" does not include the object 7 of interest. This segmentation can be done manually using any of various ordinary image editing tools (e.g. Adobe Photoshop). It may also be done automatically or semi-automatically with some vary effectiveness depending on the tool or algorithm used and the nature of the raw images. There are many known automated and semi-automated methods for image segmentation which may be suitable.

It should be noted that sometimes a tile may contain multiple appearances of the object of interest (e.g. from different perspectives) and in that case the post-processing would separate or segment one selected "primary" appearance from the tile and separate and discard any additional "ghost" or "secondary" appearances. The rest of the comments on manual or (semi-)automated segmentation below still apply.

Through the above, references to a bi-directional reflectance distribution function (BRDF), a bidirectional texture function (BTF), an 8 dimension reflectance field and/or a bi-directional scattering surface texture function (BSSTF) may mean one or more values of a bi-directional reflectance distribution function (BRDF), a bidirectional texture function (BTF), an 8 dimension reflectance field and/or a bi-directional scattering surface texture function (BSSTF). Determining or obtaining such functions or fields may also be understood to mean determining or obtaining one or more values of such functions or fields Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

APPENDIX, all of which are incorporated by reference herein.

REFERENCES

CHEN, W.-C., BOUGUET, J.-Y., CHU, M. H., AND GRZESZCZUK, R. 2002. Light field mapping: Efficient representation and hardware rendering of surface light fields. In SIGGRAPH 2002 Conference Proceedings, ACM Press/ACM SIGGRAPH, J. Hughes, Ed., Annual Conference Series, SIGGRAPH, 447-456.

DEBEVEC, P., HAWKINS, T., TCHOU, C., DUIKER, H. P., SAROKIN, W., AND SAGAR, M. 2000. Acquiring the Reflectance Field of a Human Face. In *Proceedings of ACM SIGGRAPH* 2000, ACM Press/ACM SIGGRAPH, New York. Computer Graphics Proceedings, Annual Conference Series, ACM, 145-156.

DEBEVEC, P., WENGER, A., TCHOU, C., GARDNER, A., WAESE, J., AND HAWKINS, T. 2002. A Lighting Reproduction Approach to Live-Action Compositing. *ACM Transactions on Graphics*, 21, 3, 547-556.

GARDNER, A., TCHOU, C., HAWKINS, T., DEBEVEC, P. Linear Light Source Reflectometry. ACM Transactions on Graphics (SIGGRAPH 2003). 22(3), pp. 749-758, 2003.

GORTLER, S. J., GRZESZCZUK, R., SZELISKI, R., AND COHEN, M. F. 1996. The lumigraph. In SIGGRAPH 96, Computer Graphics Proceedings, Addison Wesley, H. Rushmeier, Ed., Annual Conference Series, ACM SIGGRAPH, 43-54.

HAWKINS, T., COHEN, J., AND DEBEVEC, P. 2001. A photometric approach to digitizing cultural artifacts. In In 2nd International Symposium on Virtual Reality, Archaeology, and Cultural Heritage, Glyfada, Greece, November 2001.

JENSEN, H. W., MARSCHNER, S. R., LEVOY, M., AND HANRAHAN, P. 2001. A Practical Model for Subsurface Light Transport. In *Proceedings of* ACM SIGGRAPH 2001, ACM Press/ACM SIGGRAPH, New York.

E. Fiume, Ed., Computer Graphics Proceedings, Annual Conference Series, ACM, 511-518. LEVOY, M., AND HANRAHAN, P. 1996. Light field rendering. In SIGGRAPH 96 Conference Proceedings, Addison Wesley, H. Rushmeier, Ed., Annual Conference Series, ACM SIGGRAPH, 31-42.

LEVOY, M. Personal communication. 2000 MATUSIK, W., PFISTER, H., NGAN, A., BEARDSLEY, P., ZIEGLER, R., AND MCMILLAN, L. 2002. Image-based 3D photography using opacity hulls. In SIGGRAPH 2002 Conference Proceedings, ACM Press/ACM SIGGRAPH, J. Hughes, Ed., Annual Conference Series, SIGGRAPH, 427-437.

MATUSIK, W., PFISTER, H., ZIEGLER, R., NGAN, A., AND MCMILLAN, L. 2002. Acquisition and rendering of transparent and refractive objects. In Rendering Techniques EG 2002, Annual Conference Series, EG, 267-277.

NICODEMUS, F. E., RICHMOND, J. C., AND HSIA, J. J. 1977. Geometric Considerations and Nomenclature for Reflectance, *U.S. Dept. of Commerce, National Bureau of Standards*, October 1977.

UNGER, J., WENGER, A., HAWKINS, T., GARDNER, A., AND DEBEVEC, P. Capturing and Rendering with Incident Light Fields, Eurographics Symposium on Rendering: 14th Eurographics Workshop on Rendering. pp. 141-149, June 2003.

What is claimed is:

1. An apparatus for obtaining reflectance data of an object comprising:
a diffuser having a surface; and
a mapping portion that effects a bidirectional mapping between a light field at the object's surface and a light field at the diffuser surface for BRDF capture of the object, the mapping portion includes a kaleidoscope and a lenslet array which forms an image of at least a portion of the object surface on the diffuser surface.

2. An apparatus as described in claim 1 wherein the kaleidoscope has a top aperture with an area and the array covers at least a portion of the area of the aperture.

3. An apparatus as described in claim 2 including a digital camera that records the image on the diffuser.

4. An apparatus as described in claim 3 including a light source to illuminate at least a portion of the object through the mapping portion.

5. An apparatus as described in claim 4 wherein the lenslets of the lenslet array are placed sparsely so there are spaces between them through which light is sent into the kaleidoscope.

6. An apparatus as described in claim 5 wherein the kaleidoscope is tapered.

7. An apparatus as described in claim 6 wherein the diffuser is non-back scattering.

8. An apparatus as described in claim 7 wherein the light source is a pattern projector.

9. An apparatus as described in claim 8 including a beam splitter portion in optical alignment between the camera and the pattern projector.

10. An apparatus as described in claim 9 wherein the pattern projector produces light and dark patterns onto the diffuser.

11. An apparatus as described in claim 7 wherein the light source is a polarized light source.

12. An apparatus as described in claim 11 wherein the diffuser is a non-polarization preserving diffuser.

13. An apparatus as described in claim 12 including a polarization patterned film disposed over the diffuser.

14. An apparatus as described in claim 13 wherein the apparatus is handheld.

15. A method for obtaining reflectance data usable to determine a plurality of values of the BRDF of an object comprising the steps of:
illuminating at least a portion of the object with light passing through a kaleidoscope; and
effecting a mapping between a light field at the object's surface and a light field at a diffuser surface for BRDF capture of at least a portion of the object with a mapping portion.

16. A method as described in claim 15 wherein the effecting step includes the step of forming an image of at least a portion of the object on an area of the diffuser surface.

17. A method as described in claim 16 wherein the effecting step includes a step of recording at least a portion of the image on the diffuser surface with a digital camera to capture a plurality of values of the BRDF of the object.

18. A method as described in claim 17 wherein the illuminating step includes the step of illuminating at least a portion of the object with light passing through the kaleidoscope and a lenslet array which forms an image of at least a portion of the object surface on the diffuser surface.

19. A method as described in claim 18 wherein the illuminating step includes the step of illuminating at least a portion of the object with a pattern projector that produces light and dark patterns onto the diffuser.

20. A method as described in claim 19 wherein the illuminating step includes the step of illuminating the diffuser with light passing through a polarization patterned film.

21. An apparatus for measuring an 8D reflectance field of an object comprising:
a kaleidoscope having an opening;
one or more projectors which illuminates at least a portion of the object with light passing through the kaleidoscope;
a plurality of cameras dispersed in a staggered arrangement relative to the opening of the kaleidoscope to take images of at least a portion of the surface of the object through the kaleidoscope; and
a computer connected to the plurality of cameras for measuring 8D reflectance field of the object.

22. An apparatus as described in claim 21 wherein the plurality of cameras includes a first camera, a second camera, a third camera, and a fourth camera.

23. An apparatus as described in claim 22 wherein the kaleidoscope has a plurality of mirrors, and wherein the first camera is placed over the center of the opening, pointing straight into the kaleidoscope along a normal axis of the kaleidoscope, and the second and the third and the fourth cameras are tilted away from the normal axis of the kaleidoscope and shifted in position halfway toward a mirror of the plurality of mirrors of the kaleidoscope.

24. An apparatus as described in claim 23 wherein the projector sequentially illuminates different portions of the objects surface.

25. An apparatus as described in claim 24 including a computer in communication with the projector and the cameras to control the projector and the cameras.

26. An apparatus as described in claim 25 wherein the projector is a digital projector.

27. An apparatus as described in claim 26 wherein the area of the surface of the object is divided into a grid by the computer and a plurality of portions of the grid are selectively illuminated by the projector.

28. An apparatus as described in claim 27 wherein each camera takes an image of the portion of the grid when the portion is illuminated.

29. An apparatus as described in claim 28 wherein the grid is an 8×8 grid of 64 squares where each portion is a square of the grid, and the projector selectively illuminates each of the 64 squares of the grid in turn.

30. An apparatus as described in claim 29 including a second projector which illuminates the object with light passing through the kaleidoscope.

31. A method for measuring an 8D reflectance field of an object comprising the steps of:
    illuminating at least a portion of the object with light from one or more projectors passing through a kaleidoscope having an opening;
    taking images of at least a portion of the surface of the object through the kaleidoscope with a plurality of cameras dispersed in a staggered arrangement relative to an opening of the kaleidoscope; and
    measuring 8D reflectance field of the object using the taken images.

32. A method as described in claim 31 wherein the illuminating step includes the step of illuminating sequentially with the projector different portions of the objects surface.

33. A method as described in claim 32 wherein the kaleidoscope has a plurality of mirrors, and wherein the taking step includes the step of taking with a first camera placed over the center of the opening, pointing straight into the kaleidoscope along a normal axis of the kaleidoscope an image of the object, and with the second and the third and the fourth cameras tilted away from the normal axis of the kaleidoscope and shifted in position halfway toward a mirror of the plurality of mirrors of the kaleidoscope, respective images of the object.

34. A method as described in claim 33 wherein the illuminating step includes the step of illuminating selectively with by projector each portion of a grid of the area of the surface of the object which is divided into the grid by a computer in communication with the projector and the cameras.

35. A method as described in claim 34 wherein the taking step includes the step of taking with each camera an image of the portion of the grid when the portion is illuminated.

36. A method as described in claim 35 wherein the grid is an 8×8 grid of 64 squares where each portion is a square of the grid, and the illuminating step includes the step of illuminating with the projector selectively each of the 64 squares of the grid in turn.

37. An apparatus for measuring a plurality of values of a reflectance field of an object comprising:
    a kaleidoscope having an opening;
    one or more projectors which illuminate at least a portion of the object with light passing through the kaleidoscope;
    a plurality of cameras dispersed in a staggered arrangement relative to the opening of the kaleidoscope to take images of at least a portion of the surface of the object through the kaleidoscope; and
    a computer connected to the plurality of cameras for measuring a plurality of values of the reflectance field of the object.

38. The apparatus of claim 37 wherein at least a portion of the cameras are angularly staggered relative to the opening of the kaleidoscope.

39. The apparatus of claim 37 wherein a plurality of projectors are staggered relative to a reference projector or the opening of the kaleidoscope.

40. The apparatus of claim 39 where the plurality of projectors are angularly staggered relative to a reference projector or the opening of the kaleidoscope.

* * * * *

UNITED STATES PATENT AND TRADEMARK OFFICE
CERTIFICATE OF CORRECTION

PATENT NO. : 7,830,522 B2  
APPLICATION NO. : 11/705195  
DATED : November 9, 2010  
INVENTOR(S) : Jefferson Y. Han et al.

Page 1 of 1

It is certified that error appears in the above-identified patent and that said Letters Patent is hereby corrected as shown below:

On the Title Page, Item (60), delete "Provisional application No. 60/476,320 filed on Jun. 6, 2003,".

In the Specification

Column 1, lines 5 and 6, delete "This application claims the benefit of U.S. Provisional Application No. 60/476,320 filed on Jun. 6, 2003.".

Signed and Sealed this  
First Day of October, 2013

Teresa Stanek Rea  
*Deputy Director of the United States Patent and Trademark Office*